United States Patent [19]

Beck et al.

[11] Patent Number: 5,041,686

[45] Date of Patent: Aug. 20, 1991

[54] PROCESS FOR THE PREPARATION OF CARBONYL COMPOUNDS

[75] Inventors: Horst-Philipp Beck, Dudweiler/Saar; Gerhard Emig, Erlangen; Günther Wiesgickl, Grosswallstadt; Karlheinz Burg; Karl-Friedrich Mück, both of Wiesbaden, all of Fed. Rep. of Germany

[73] Assignee: Hoechst Aktiengesellschaft, Frankfurt am Main, Fed. Rep. of Germany

[21] Appl. No.: 546,034

[22] Filed: Jun. 29, 1990

[30] Foreign Application Priority Data

Jun. 30, 1989 [DE] Fed. Rep. of Germany ....... 3921452

[51] Int. Cl.$^5$ .............................................. C07C 45/29
[52] U.S. Cl. ...................................... 568/473; 568/472
[58] Field of Search .............................. 568/473, 472

[56] References Cited

U.S. PATENT DOCUMENTS

| | | | |
|---|---|---|---|
| 4,098,826 | 7/1978 | Alper et al. | 568/473 |
| 4,198,351 | 4/1980 | Braneck et al. | 568/473 |
| 4,208,353 | 6/1980 | Webster et al. | 568/473 |
| 4,306,089 | 12/1981 | Webster et al. | 568/473 |
| 4,359,587 | 11/1982 | Abdurakhanou | 568/473 |
| 4,786,743 | 11/1988 | Bongaarts | 568/473 |

FOREIGN PATENT DOCUMENTS

| | | | |
|---|---|---|---|
| 2816471 | 10/1978 | Fed. Rep. of Germany . | |
| 3037536 | 7/1986 | Fed. Rep. of Germany . | |
| 113173 | 5/1975 | German Democratic Rep. . | |
| 0108524 | 8/1981 | Japan | 568/472 |
| 1130252 | 6/1986 | Japan | 568/472 |
| 0662544 | 5/1979 | U.S.S.R. | 568/472 |
| 1603821 | 12/1981 | United Kingdom . | |

*Primary Examiner*—Werren B. Lone

[57] ABSTRACT

A process for the preparation of carbonyl compounds by the oxydehydrogenation of ($C_1$–$C_4$)-alcohols is carried out at a temperature from 400° to 700° C. in the presence of a silicate catalyst which has been doped with silver and silver ions. By means of the process carried out at relatively low temperatures, for example, are that high yields are achieved, the content of carbon monoxide is low and the product gas contains, apart from carbon dioxide, no further determinable by-products and has a low water/formaldehyde ratio.

10 Claims, No Drawings

PROCESS FOR THE PREPARATION OF CARBONYL COMPOUNDS

The invention relates to a process for the preparation of carbonyl compounds by the oxydehydrogenation of ($C_1$–$C_4$)-alcohols at a temperature from 400° to 700° C. in the presence of a silicate catalyst which has been doped with silver and silver ions.

Skeleton silicate catalysts, for example zeolites, are already employed on a large industrial scale as catalysts for the non-oxidative conversion of hydrocarbons, for example in catalytic cracking.

It is also known that organic compounds can be oxidized selectively by means of zeolite catalysts, as is the case, for example, in the manufacture of acetone from propene. In this case a selectivity of 90% is achieved at a conversion of 50%. No statements are made concerning the long-term activity and the aging behavior of the catalysts used.

It is also assumed that, because of their special structure, zeolites tend to accelerate the total oxidation of organic compounds to $CO_2$ and water.

The preparation of certain catalysts based on zeolites is described in East German Patent 113,173. In this case certain metals, such as vanadium and/or titanium, are incorporated into the zeolites by ion exchange.

A "silver-on-pumice" or "silver-on-$Al_2O_3$" catalyst is frequently used for the oxydehydrogenation reactions of $C_1$–$C_4$-alcohols, for example of methanol to give formaldehyde, which are of particular industrial importance. The preparation of a silver catalyst synthesized by impregnating the support, composed of $Al_2O_3$ and $SiO_2$ in the form of cristobalite, with silver nitrate solution is discussed in German Patent 3,037,536. A catalyst composed of a metal or ceramic support which has been coated or impregnated with metallic copper, silver, gold or iron (German Offenlegungsschrift 2,816,471) is also described for the preparation of formaldehyde from methanol.

However, the catalysts mentioned, which are employed in processes for the preparation of carbonyl compounds by the oxidative dehydrogenation of $C_1$–$C_4$-alcohols, give only relatively low yields of end product, relative to the throughput and conversion of raw material; in addition the degree of conversion of the raw material and the quality of the products is still unsatisfactory in most cases. Formic acid is also frequently formed as an undesirable by-product in the known processes. It was therefore the object to improve further the process for the preparation of oxo compounds.

The process for the oxydehydrogenation of ($C_1$–$C_4$)-alcohols is used, for example, in the preparation of formaldehyde from methanol, of acetone from isopropanol and of methyl ethyl ketone from secondary butanol.

Formaldehyde is an important raw material for industry. It is used, for example, as a disinfectant and deodorant. It is also a starting material for numerous syntheses in the chemical industry and is mainly used for the manufacture of plastics and pharmaceutical formulations. In addition it is also used in the dyestuffs and auxiliaries industry.

The invention relates to a process for the preparation of carbonyl compounds by reacting ($C_1$–$C_4$)-alcohol in the presence of oxygen using a catalyst at an elevated temperature, in which process the reaction is carried out at a temperature from 400° to 700° C., preferably 500° to 600° C., in the presence of a catalyst composed of a silicate complex containing silver halide and elementary silver. The catalyst is characterized by the formula $$M_{2/n}O \cdot v\ Ag^0 \cdot w\ AgX \cdot Al_2O_3 \cdot x\ SiO_2 \cdot y\ H_2O \qquad (1)$$

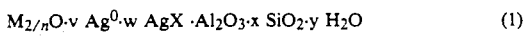

in which M denotes a metal atom of valence n, $Ag^0$ denotes elementary silver, X denotes a halogen atom, preferably chlorine or bromine, and v, w, x and y denote stoichiometric coefficients. The catalyst preferably has the formula $$Na_2O \cdot 1.4\ Ag \cdot 0.4\ AgCl \cdot Al_2O_3 \cdot 2.47\ SiO_2 \cdot 3.9\ H_2O \qquad (2)$$

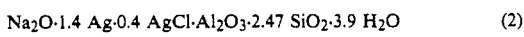

The preparation of the silicate catalysts employed is described in German Patent Application P 39 21 450.8, entitled: "Catalyst for selective oxidation reactions", which has been filed on the same day and to which reference is hereby made. The catalyst has a particle size of 0.5 to 5 mm, preferably 0.5 to 2 mm.

The process according to the invention is carried out by mixing and preheating the gaseous starting components and then feeding them to the vaporizer. The alcohol component is also passed into the vaporizer at the same time. The gas mixture thus formed is then passed through the reactor in which the catalyst is located, heated to a temperature of 400° to 700° C., preferably 500° to 600° C. Compared with those for the process using catalysts composed of pure silver, the reaction temperatures are markedly lower.

The customary materials hitherto known are suitable as a material for the design of the reactor. However, the use of quartz glass has proved to be particularly advantageous.

The arrangement of the catalyst in the apparatus can be carried out in accordance with known methods. It is advantageous to use a fixed bed reactor in which steps are taken to ensure that the discharge of very fine catalyst particles by the gas stream is prevented in a suitable manner.

Aliphatic alcohols having 1 to 4 carbon atoms in the alkyl group, for example methanol, isopropanol and secondary butyl alcohol, are suitable for conversion into carbonyl compounds in the process according to the invention. The oxidative dehydrogenation takes place in the presence of oxygen. This should also be understood as meaning that air is employed as the oxidizing medium. If pure oxygen is employed, it is appropriate to use an inert gas, preferably nitrogen, in addition.

As a result of the process according to the invention the conversion of $C_1$–$C_4$-alcohols is increased surprisingly and it affords carbonyl compounds with an improved selectivity and yield.

The measurable variables indicated in the examples were calculated as follows:

$$\text{Conversion (in \%)} = \frac{\text{methanol converted (mol)}}{\text{methanol metered in (mol)}} \times 100$$

$$\text{Yield (in \%)} = \frac{\text{formaldehyde formed (mol)}}{\text{methanol metered in (mol)}} \times 100$$

$$\text{Selectivity (in \%)} = \frac{\text{formaldehyde formed (mol)}}{\text{methanol converted (mol)}} \times 100$$

By means of the process carried out at relatively low temperatures, for example, high yields are achieved, the content of carbon monoxide is low and the product gas contains, apart from carbon dioxide, no further determinable by-products and has a low water/formaldehyde ratio.

EXAMPLES

Preparation of the catalysts 1) 10.71 g of zeolite 13X (formula $Na_2O \cdot Al_2O_3 \cdot 2.47 SiO_2 \cdot 3.9 H_2O$) were put into a beaker, 500 ml of 0.1 N $AgNO_3$ solution were added and the mixture was stirred vigorously for 4 hours with the exclusion of light. After filtration, the residue was washed with 50 ml of water and a further 400 ml of 0.1 N silver nitrate solution were added, the mixture was stirred for 4 hours with the exclusion of light and then filtered and the resulting solid substance was dried in the air. 7.88 g of this substance were freed from water under reduced pressure at 350° C. and were then subjected to reductive treatment with hydrogen under a pressure of 0.6 bar for 20 minutes at the same temperature. The hydrogen was then removed and the residue was cooled to 270° C. The solid substance was then treated in oxygen (0.67 bar) for 8 minutes at this temperature and, after the oxygen had been removed, was cooled to approx. 25° C. 3.5 g of the substance obtained were suspended in 200 ml of water, and 5 ml of concentrated hydrochloric acid were added with stirring. Five minutes later 25 ml of half-concentrated ammonia solution (7 mol/liter) and 17 g of sodium nitrate were metered in. This suspension was stirred for 1 hour and then filtered, and the residue was washed with a total of 200 ml of water. The substance obtained was dried in the air and compressed into pellets of 6 mm diameter, which were subsequently comminuted.

2) 8.51 g of zeolite 13X (formula: $Na_2O \cdot Al_2O_3 \cdot 2.47 SiO_2 \cdot 3.9 H_2O$) were put into a beaker, 400 ml of 0.1 N $AgNO_3$ solution were added and the mixture was stirred vigorously for 3 hours with the exclusion of light. After filtration, the residue was washed with 50 ml of water and a further 400 ml of 0.1 N silver nitrate solution were added, the mixture was stirred for 3 hours with the exclusion of light and then filtered, and the resulting solid substance was dried in the air. 6.35 g of this substance were freed from water under reduced pressure at 330° C. and were then reduced for 25 minutes with pure hydrogen under a pressure of 0.67 bar. The substance was then cooled to 170° C. under reduced pressure, oxidized with chlorine under a pressure of 0.6 bar for 30 minutes and cooled to room temperature under reduced pressure. 4 g of the substance thus obtained were suspended in 200 ml of water, and 20 g of sodium nitrate and 30 ml of half-concentrated ammonia solution were metered in. This suspension was stirred for 20 minutes and then filtered and the residue was washed with a total of 250 ml of water. The substance obtained was dried in the air and compressed into pellets of 6 mm diameter, which were subsequently comminuted.

3) (Comparison 1) 6.7 g of zeolite 13X (formula: $Na_2O \cdot Al_2O_3 \cdot 2.47 SiO_2 \cdot 3.9 H_2O$) were put into a beaker, 300 ml of 0.1 N $AgNO_3$ solution were added and the mixture was vigorously stirred for 4 hours with the exclusion of light. After filtration, the residue was washed with 50 ml of water and a further 300 ml of 0.1 N silver nitrate solution were added, mixing was carried out for 4 hours with the exclusion of light and the mixture was then filtered and the resulting solid substance was dried in the air. 7.5 g of this substance were freed from water under reduced pressure at 350° C. and were then subjected to reductive treatment with hydrogen under a pressure of 0.6 bar for 20 minutes at the same temperature.

After the pressure had been reduced, the resulting substance was cooled to room temperature and suspended in 200 ml of water, and 25 ml of half-concentrated ammonia solution (7 mol/liter) and 15 g of sodium nitrate were added. This suspension was stirred and then filtered, and the residue was washed with a total of 100 ml of water. The substance obtained was dried in the air and compressed into pellets of 6 mm diameter, which were subsequently comminuted.

4) (Comparison 2) Comparison catalyst 2 is composed of approximately spherical, electrolytically deposited silver having a particle diameter of $1 \pm 0.5$ mm.

5) A particle size fraction of 1 mm $\pm 0.5$ was selected from each of the catalysts of Examples 1 to 4 for the conversion of methanol into formaldehyde by the process according to the invention. Each of the catalysts was placed in a quartz tube of internal diameter 12 mm, which was heated to the reaction temperatures stated, the bed depth of the catalyst being the same in Examples 1 and 4. The gaseous starting materials were metered in in the amounts indicated in the table and were mixed and preheated, and then passed to a vaporizer upstream of the reaction section. The amounts of methanol employed in each case were also passed into the vaporizer at the same time. The gas mixture thus formed was passed through the reaction tube.

The product gas was analyzed by gas chromatography. The corresponding data and results are collated in the table below, the oxygen conversion always being 100%.

The following abbreviations are used in the table:
Cat.: catalyst
Wt. Cat.: weight of catalyst used
T: reaction temperature
Me: methanol
$N_2$: nitrogen
$O_2$: oxygen
Conv.: conversion of methanol
Yld.: yield of formaldehyde
Sel.: selectivity to formaldehyde
Fa: formaldehyde
$H_2O/Fa$: water/formaldehyde ratio in the product gas

TABLE

| Cat. (Example) | Wt. Cat. (g) | T (°C.) | Mol (Me/h) (mol/h) | Mol ($N_2$/h) (mol/h) | Mol ($O_2$/h) (mol/h) | Conv. (%) | Yld. (%) | Sel. (%) | $H_2O/Fa$ (mol/mol) |
|---|---|---|---|---|---|---|---|---|---|
| 1 | 1.00 | 550 | 0.379 | 3.467 | 0.0381 | 33.5 | 32.5 | 97.0 | 0.645 |
| " | " | " | " | 3.437 | 0.0665 | 51.9 | 50.4 | 97.1 | 0.658 |
| " | " | " | " | 3.414 | 0.0871 | 64.3 | 61.4 | 95.4 | 0.735 |
| " | " | " | 0.380 | 3.384 | 0.117 | 76.3 | 69.6 | 91.3 | 0.790 |
| " | " | 600 | 0.358 | 3.265 | 0.0358 | 32.0 | 31.9 | 99.6 | 0.679 |
| " | " | " | " | 3.241 | 0.0627 | 52.2 | 51.1 | 97.9 | 0.667 |

TABLE -continued

| Cat. (Example) | Wt. Cat. (g) | T (°C.) | Mol (Me/h) (mol/h) | Mol (N$_2$/h) (mol/h) | Mol (O$_2$/h) (mol/h) | Conv. (%) | Yld. (%) | Sel. (%) | H$_2$O/Fa (mol/mol) |
|---|---|---|---|---|---|---|---|---|---|
| " | " | " | — | 3.218 | 0.0835 | 64.5 | 62.4 | 96.7 | 0.725 |
| " | " | " | " | 3.194 | 0.1105 | 76.8 | 72.7 | 94.7 | 0.792 |
| 4 (Comp. 2) | 5.66 | 550 | 0.379 | 3.467 | 0.0381 | 25.4 | 24.8 | 97.6 | 0.858 |
| " | " | " | " | 3.437 | 0.0665 | 40.8 | 38.8 | 95.1 | 0.863 |
| " | " | " | 0.380 | 3.414 | 0.0871 | 50.7 | 47.3 | 93.2 | 0.898 |
| " | " | " | " | 3.384 | 0.117 | 62.0 | 55.0 | 88.7 | 0.931 |
| " | " | 600 | 0.358 | 3.265 | 0.0358 | 29.3 | 29.1 | 99.3 | 0.759 |
| " | " | " | " | 3.421 | 0.0627 | 47.2 | 45.9 | 97.2 | 0.760 |
| " | " | " | " | 3.218 | 0.0835 | 60.1 | 55.3 | 91.9 | 0.789 |
| " | " | " | " | 3.194 | 0.1105 | 71.9 | 63.0 | 87.7 | 0.859 |
| 2 | 1.65 | 550 | 0.397 | 3.496 | 0.795 | 55.5 | 53.5 | 96.4 | 0.677 |
| " | " | 600 | " | 3.414 | 0.159 | 85.1 | 76.4 | 89.8 | 0.782 |
| 3 (Comp. 1) | 1.52 | 550 | 0.397 | 3.496 | 0.0795 | 55.1 | 52.7 | 95.8 | 0.686 |
| " | " | 600 | " | 3.414 | 0.159 | 87.6 | 75.6 | 86.3 | 0.807 |

It can be seen from the table that when the complex silicate catalysts in accordance with the process according to the invention are employed, the conversion of methanol and the yield of formaldehyde and selectivity to formaldehyde increase compared with the catalysts employed as a comparison. Furthermore, the water/formaldehyde ratio in the product gas is clearly shifted in favor of the silver-doped silicate catalysts employed in the process according to the invention. The increased activity of these catalysts compared with a spherical silver catalyst according to Example 4 (Comparison 2) is also particularly striking.

We claim:

1. A process for the preparation of carbonyl compounds by reacting (C$_1$–C$_4$)-alcohols in the presence of oxygen using a catalyst at an elevated temperature, which comprises carrying out the reaction at a temperature from 400° to 700° C. in the presence of a catalyst composed of a silicate complex containing silver halide and elementary silver.

2. The process as claimed in claim 1, wherein the reaction is carried out at 500° to 600° C.

3. The process as claimed in claim 1, wherein methanol is reacted.

4. The process as claimed in claim 1, wherein the catalyst employed is a skeleton silicate complex of the formula

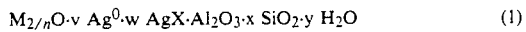

$$M_{2/n}O \cdot v\ Ag^0 \cdot w\ AgX \cdot Al_2O_3 \cdot x\ SiO_2 \cdot y\ H_2O \quad (1)$$

in which M denotes a metal atom of elements of groups I and II of valence n, Ag$^0$ denotes elementary silver, X denotes a halogen atom and v, w, x and y denote stoichiometric coefficients.

5. The process as claimed in claim 1, wherein the catalyst employed is a skeleton silicate complex of the formula

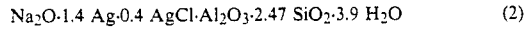

$$Na_2O \cdot 1.4\ Ag \cdot 0.4\ AgCl \cdot Al_2O_3 \cdot 2.47\ SiO_2 \cdot 3.9\ H_2O \quad (2)$$

6. The process as claimed in claim 1, wherein the reaction is carried out in the presence of an inert gas.

7. The process as claimed in claim 6, wherein the inert gas employed is nitrogen.

8. The process as claimed in claim 1, wherein an alcohol/air mixture is reacted.

9. The process as claimed in claim 1, wherein the catalyst is used in the form of approximately spherical particles having diameters within the range from 0.5 to 5 mm.

10. The process as claimed in claim 4, wherein M denotes sodium and X denotes bromine and chlorine.

* * * * *